United States Patent [19]
Vogel et al.

[11] Patent Number: 6,101,417
[45] Date of Patent: Aug. 8, 2000

[54] IMPLANTABLE ELECTRICAL DEVICE INCORPORATING A MAGNETORESISTIVE MAGNETIC FIELD SENSOR

[75] Inventors: Alan Vogel, Saugus; Ken McNeil, II, Valencia, both of Calif.

[73] Assignee: Pacesetter, Inc., Sylmar, Calif.

[21] Appl. No.: 09/076,351

[22] Filed: May 12, 1998

[51] Int. Cl.[7] .................................................. A61N 1/37
[52] U.S. Cl. .............................................................. 607/30
[58] Field of Search ................................ 607/30, 32, 60; 128/903; 324/258, 253, 654

[56] References Cited

U.S. PATENT DOCUMENTS

| | | | |
|---|---|---|---|
| 4,541,431 | 9/1985 | Ibrahim et al. | 607/30 |
| 5,052,388 | 10/1991 | Sivula et al. | |
| 5,292,342 | 3/1994 | Nelson et al. | |
| 5,529,578 | 6/1996 | Struble. | |
| 5,545,187 | 8/1996 | Bergstrom et al. | 607/32 |
| 5,562,714 | 10/1996 | Grevious. | |
| 5,694,952 | 12/1997 | Lidman et al. | 128/899 |
| 5,764,052 | 6/1998 | Renger | 324/258 |
| 5,873,733 | 2/1999 | Paul et al. | 434/262 |

FOREIGN PATENT DOCUMENTS

1769852A1  10/1992  U.S.S.R. .

OTHER PUBLICATIONS

Driller J. and Parsonnet, V., "The magnetic reed switch in pacemaker mode switching", Med. Instrument., vol. 8 (1974), pp. 316–321.

NonVolatile Electronics, Inc. Brochure "Integrated GMR Magnetic Sensors".

Primary Examiner—Jeffrey R. Jastrzab

[57] ABSTRACT

An implantable electrical device that includes a control unit and one or more leads. The leads are configured to be implanted in the chambers of the heart of a patient and the control unit is configured to be implanted in the body of the patient. The control unit induces the leads to provide therapeutic electrical stimuli to the heart. The control unit also includes a magnetoresistive sensor that senses the presence of an externally applied magnetic field. The sensor outputs a signal which has a value that is proportionate to the sensed magnitude of the externally applied magnetic field. The control unit initiates a preprogrammed activity, which for example can be either a function or a change in the mode of operation of the device, when it receives a signal from the magnetic field sensor indicating that the magnitude of the sensed magnetic field has a value corresponding to the magnitude of a magnetic field that occurs as a result of positioning a selected external magnet adjacent the control unit.

15 Claims, 4 Drawing Sheets

IMPLANTABLE ELECTRICAL DEVICE INCORPORATING A MAGNETORESISTIVE MAGNETIC FIELD SENSOR

FIELD OF THE INVENTION

The present invention relates to implantable electrical devices and, in particular, concerns an implantable electrical device which incorporates a magnetoresistive magnetic field sensor which can be triggered by the application of an external magnetic field to thereby induce the implantable electrical device to initiate a preselected activity such as initiate a particular function or initiate a different mode of operation.

BACKGROUND OF THE INVENTION

Implantable electrical devices, such as pacemakers and intra-cardioverter defibrillators have become increasingly sophisticated over the last decade. These types of implantable electrical devices typically have a control unit and one or more leads which are implanted in or around the heart. The control unit induces the one or more leads to deliver a therapeutic electrical stimulus to the heart. Generally, the control unit is positioned within a casing that is configured to be positioned within the body of the patient. One typical place for implantation of the casing is under the patient's pectoral muscle, i.e., a pectoral implant.

The control units generally incorporate a power supply, a processor and several sensors. The sensors provide the processor with pertinent information to allow the processor to induce the leads to apply appropriate therapeutic stimuli to the heart. These sensors can include activity sensors which provide the processor with an indication of the activity level of the patient and body position sensors that provide the processor with an indication of the orientation of the patient. Further, it is common to have a sensor positioned adjacent the wall of the heart to provide the processor with signals indicative of the activity of the heart. Typically, an intracardiac electrogram (IEGM) is provided by this sensor to the processor. All of this information is then used by the processor to determine whether to apply an electrical therapeutic stimulus to the heart and is also used to determine the configuration of the applied stimulus.

One example of a sophisticated implantable electrical device is a demand-type pacemaker which senses the intrinsic activity of the heart and is then provides an electrical therapeutic stimulus to the heart only when it senses an absence of an appropriate intrinsic activity of the heart. This type of pacemaker is therefore providing the stimulus to the heart only on an as-needed basis thereby minimizing the drain on the power supply and limiting the disruption of the heart's natural function. This is in contrast to a pacemaker which provides the stimulus at the heart at a fixed rate regardless of the intrinsic activity of the heart.

As the implantable electrical devices have become increasingly more sophisticated, these devices are capable of providing different therapy to the heart based upon the sensed condition. Further, these devices are also capable of storing data indicative of the sensed activity of the heart during a particular interval of time for future downloading to an external monitor. This permits subsequent evaluation of the downloaded data by the treating physician.

With the increased capability of the implantable electrical devices and, in particular, the variety of possible functions and modes of operation of the device, there has been a desire to be able to change the device's mode of operation or have it initiate new functions simply and easily. Sophisticated implantable electrical devices include telemetry circuitry which allows for communication between the implanted device and an externally monitoring system. Typically, the patient goes to a physician's office which is equipped with the external monitoring system where the monitoring system communicates with the processor, generally through the use of RF signals. This allows the physician to monitor the performance of the implantable electrical device and also allows the physician to reprogram the processor to change various performance parameters of the device.

While the telemetry circuitry greatly enhances the ability of the treating physician to program the implantable electrical device for the specific symptoms being exhibited by the patient, it does require that the patient travel to the physician's office to have the processor reprogrammed. However, there are circumstances where it is desirable to be able to change a performance parameter of the device without requiring the use of a complicated telemetry circuit.

For example, the patient may detect an abnormality in the function of either their heart or the implanted electrical device. These conditions could be either simply corrected or recorded for subsequent evaluation by the initiation of a specific pre-programmed activity performed by the device. Hence, there has been a need for some type of device that would allow the patient or physician to initiate a preprogrammed activity in the device such as a new mode of operation or a new function in a simpler manner than using a telemetry system.

To address this need, implantable electrical devices are often equipped with a reed switch which closes upon the application of an external magnetic field. Reed switches are described in some detail in an article entitled "The Magnetic Reed Switch in Pacemaker Mode Switching," by Jack Driller and Victor Parsonnet, M.D., published in *Medical Instrumentation*, Vol. 8 (1974) pp. 316–321. Specifically, the reed switch has two metal strips of a deformable magnetic material that are positioned within a glass capsule. The strips are mounted so that in the absence of an external magnetic field, the strips do not touch one another. However, when an external magnetic field is applied to the strips, the two strips bend and make contact with one another thereby closing a circuit. The switch is preferably electrically connected to the processor so that the closure of the switch in response to the applied external magnetic field is sensed by the processor thereby allowing the processor to initiate a preprogrammed activity such as a preprogrammed mode of operation or a preprogrammed function.

While reed switches enable the patient or a doctor to quickly and efficiently alter the performance of the implanted device, reed switches have several disadvantages. One disadvantage is that the reed switch may be accidentally triggered. Specifically, the patient may inadvertently be in the presence of a strong magnetic field which could trigger the reed switch. This is the result of reed switches being incapable of distinguishing between magnetic fields of different magnitudes. The strong magnetic field may be the result of the patient being around industrial equipment or undergoing a medical procedure such as magnetic resonance imaging (MRI). The inadvertent closing of the reed switch in such a circumstance may result in the implantable electrical device switching to an undesired mode of operation or initiating an undesired function.

Further, a reed switch is a comparatively large component. The processor and control circuitry for pacemaker and intra-cardioverter defibrillator (ICD) applications is preferably as small as possible so that the invasiveness of the implanted device is reduced. However, the reed switch is often large and consumes a significant amount of the limited space within the casing containing the control circuitry.

Yet another difficulty with reed switches is that these switches can be unreliable in operation. As the function of the switch relies upon a mechanical occurrence, i.e., the mechanical movement of the two reeds in response to the applied external magnetic field, variations in the material comprising the reeds may result in variations of performance of the reed switch. Hence, application of external magnetic fields in some circumstances may not result in actuation of the reed switch in the desired fashion. Further, repeated actuation of the reed switch may result in fatigue in one of the reeds to the point where the reed may become unreliable. Additionally, the reeds may occasionally remain stuck together after the application of the external magnetic field. In this circumstance, the reed switch may be continuously inducing the processor to perform a specific function that is not needed. This can also result in the reed switch no longer being capable of sensing future applications of the applied magnetic field.

From the foregoing, it should be apparent that there is a need for an improved sensing device for use in an implantable electrical device which is capable of detecting the presence of an externally applied magnetic field. In particular, the improved sensing device should be less susceptible to inadvertently applied magnetic fields and should be more reliable. To this end, there is a need for a non-mechanically activated magnetic field sensor that is small in size and can be implanted within the body of a patient so as to provide the implantable electrical device's processor with a signal indicative of the application of a specific preselected externally applied magnetic field.

SUMMARY OF THE INVENTION

The aforementioned needs are satisfied by the implantable electrical device of the present invention which is comprised of a control unit that is configured to be implanted within the body of a patient, and includes a processor which received input signals from a plurality of sources. The implantable electrical device also includes at least one lead that is configured to be positioned adjacent the heart so that the control unit can induce the leads to apply a therapeutic electrical stimulus to the heart in response to the input signals received by the processor. The implantable electrical device also includes a sensor that provides an input signal to the processor indicative of the sensing of a preselected externally applied magnetic field. The magnetoresistive sensor preferably comprises at least one resistive element wherein the resistance of the element varies over a range of values corresponding to the magnitude of the externally applied magnetic field. The sensor then outputs a magnetic field signal which has a value, selected from a range of values, that is indicative of the magnitude of the externally applied magnetic field. The control unit can be configured so that the processor can initiate a selected preprogrammed activity in response to the magnetic field signal indicating that the sensed magnetic field corresponds to a preselected magnetic field.

Hence, in one aspect of the invention, the magnetoresistive sensor and the processor can be configured so that the processor initiates a new function or new mode of operation only when it receives an input signal from the sensor that is indicative of the presence of a magnetic field of a preselected magnitude. This reduces the likelihood that a preprogrammed activity will be inadvertently initiated as a result of the application of an extraneous magnetic field. Specifically, the threshold value for initiating activity of the processor in response to an applied external magnetic field can be selected so that it is within a range of values which would only occur as a result of the positioning of a specific external magnet adjacent the sensor. Magnetic fields that are stronger or weaker than the threshold range would not result in the processor initiating a new function or mode of operation.

In one application, the sensing of the magnetic field of the preselected magnitude results in the processor initiating a different mode of operation. For example, the processor may initiate an alternate pacing therapy as a result of the application of the magnetic field. Alternatively, the sensing of the magnetic field of the preselected magnitude may result in the processor initiating a specific preprogrammed function. For example, the processor may initiate a function whereby the sensed activity of the heart and the implantable electrical device are stored in a memory for future downloading via a telemetry circuit to an external monitor. This would allow the patient who is experiencing asymptomatic heart function or asymptomatic device function to apply the external magnetic field to induce the processor to initiate this recording function.

The magnetoresistive sensor is preferably configured so as to be positioned on a hybrid substrate that contains components of the implantable electrical device. Preferably, the magnetoresistive element is small in size so that less space is consumed by the sensor. It will be appreciated that a magnetoresistive-based sensor is more reliable than a mechanically activated reed switch as the result of the elimination of moving parts within the sensor. These and other objects and advantages of the present invention will become more fully apparent from the following description taken in conjunction with the accompanying drawings.

DETAILED DESCRIPTION OF THE PREFERRED EMBODIMENT

Figure 1:
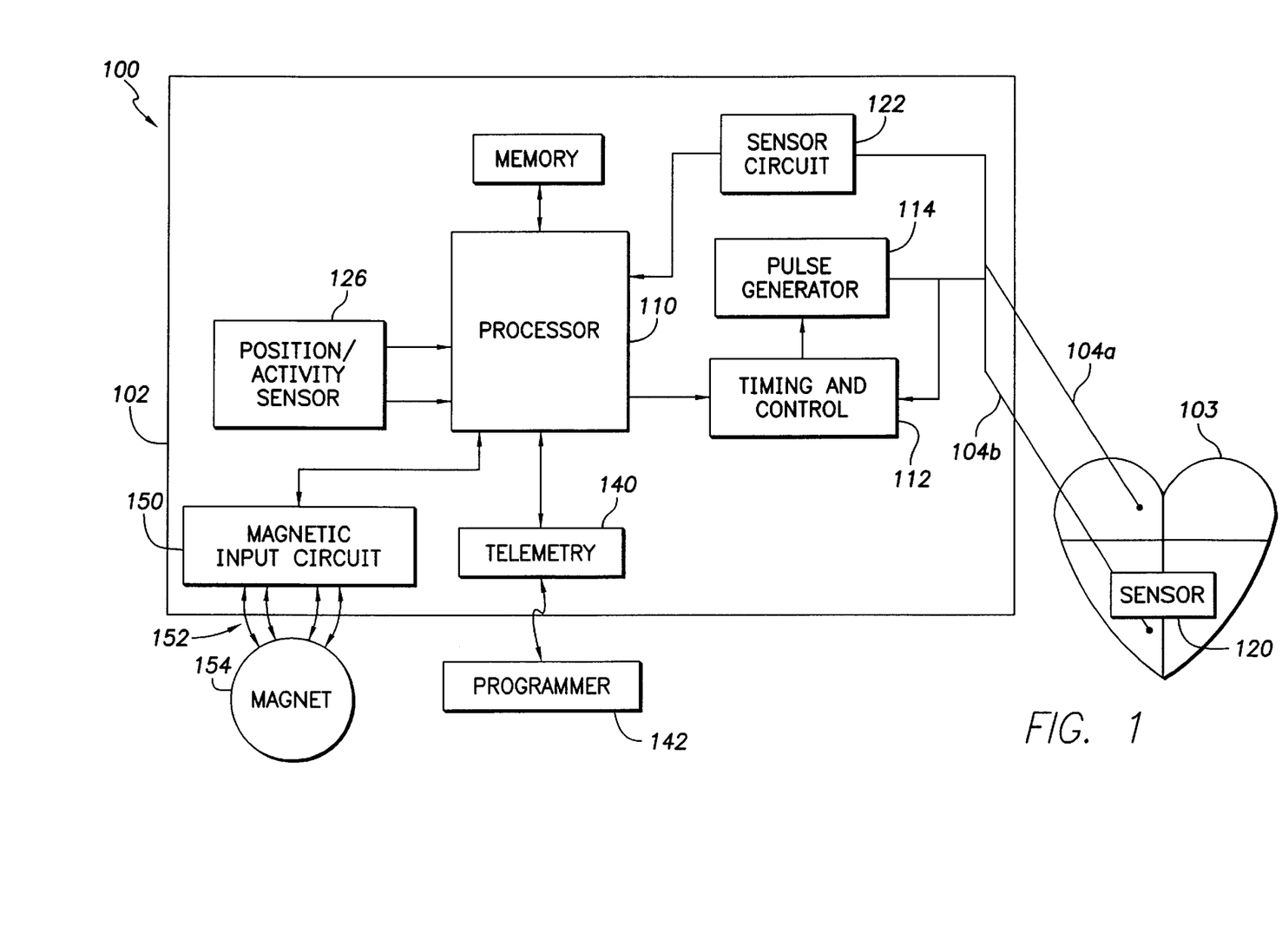
FIG. 1 is a block diagram of one embodiment of a implantable electrical device incorporating a magnetoresistive sensor.

Reference will now be made to the drawings wherein like numerals refer to like parts throughout. Referring initially to FIG. 1, one embodiment of an implantable electrical device 100 is shown. The implantable electrical device 100 incorporates a control unit, generally designated 102, and a plurality of leads 104 that are configured to be positioned within the chambers of a patient's heart 103. In the embodiment shown in FIG. 1, the implantable electrical device 100 includes a first lead 104a that is configured to be implanted within an atrium of the heart and a second lead 104b that is configured implanted within the ventricle of the heart 103.

The implantable electrical device 100 can be comprised of a pacemaker or an intra-cardioverter defibrillator or some implantable device incorporating the functionality of both a pacemaker and an intracardioverter defibrillator. The control unit 102 is preferably positioned within a casing that is also configured to be implanted within the body of the patient. In one application, the control unit 102 positioned within the casing is designed to be implanted underneath the pectoral muscle of the patient and the leads are designed to be inserted into the chambers of the heart 103 using well known techniques.

The control unit 102 includes a processor 110 which provides output signals to a timing and control circuit 112. Upon receipt of the output signals from the processor 110, the timing and control circuit 112 induces a pulse generator 114 to produce a therapeutic electrical stimulus that is transported via the leads 104 to thereby stimulate the heart 103. The exact function of the processor 110 in inducing the delivery of therapeutic electrical stimulus to the heart is performed in any of a number of well known manners.

Further, the processor 110 receives input signals from a sensor 120 via a sensor circuit 122. In one embodiment, the sensor 120 is actually comprised of an implanted lead that is positioned within one of the ventricles of the heart 103 so as to provide an intracardiac electrogram (IEGM) signal to the processor 110 in a well known manner. Hence, the processor 110 is configured to receive a signal which is indicative of the activity of the heart 103.

Further, the control unit 102 may also include additional sensors, such as a position switch 124 and an activity sensor 126, that provides the processor 110 with input signals which are indicative of the position of the patient and the activity level of the patient. The processor 110 uses the input signals from the sensor 120, the position switch 124 and the activity sensor 126 to induce the timing and control circuitry 112 and the pulse generator 114 to provide an appropriate therapeutic electrical stimulus to the heart 103 via the leads 104 in accordance with preprogrammed instructions.

For example, the processor 110 may be configured to detect the occurrence of ventricular fibrillation and induce an ICD coil that is part of one of the leads 104 to provide an appropriate defibrillation electrical stimulus to the heart 103. Alternatively, the processor 110 may be configured to provide pacing stimulus to the heart 103 via the leads 104 in response to sensed intrinsic activity of the heart from the sensor 120 and also in response to position and activity signals from the position switch 124 and the activity sensor 126. The control unit 102 also preferably includes a memory 130 that has stored data and instructions that are accessible by the processor 110.

The processor 110 of the embodiment shown in FIG. 1 is also capable of communicating via a telemetry circuit 140 with an external programmer 142. As is understood in the art, the telemetry circuit 140 includes an RF signal generator and an RF signal receiver that communicates with a matching RF signal generator and RF signal receiver on the programmer 142. Instructions can be downloaded into the processor 110 to configure the processor 110 to provide particular types of therapy to the heart 103. Further, information and data stored in the memory 130 can be uploaded by the processor 110 via the telemetry circuitry 140 to the external programmer 142. This allows for treating physicians to retrieve information stored in the memory 110 indicative of the functioning of the implantable electrical device 100 or the heart 103 during particular episodes.

In all of the foregoing aspects, the function and operation of the implantable electrical device 100 is substantially the same as the function and operation of similar implantable electrical devices of the prior art. Moreover, a person of ordinary skill in the art will appreciate that the configuration of the implantable electrical device shown in FIG. 1 is simply illustrative of one possible configuration and that the exact configuration and operation of the implantable electrical device can vary without departing from the present invention.

FIG. 1 also illustrates that the implantable electrical device 100 includes a magnetic sensor circuit 150. As will be explained in greater detail below in reference to FIGS. 2 and 3, the magnetic sensor circuit 150 includes a magnetoresistive element wherein the resistance of the element changes based upon the magnitude of an applied external magnetic field. The sensor 150 is configured to produce a magnetic field signal that has a value which corresponds to the sensed magnitude of the applied magnetic field. The magnetic field signal is then processed to determine whether the sensed magnetic field is an externally applied magnetic field 152 having a preselected magnitude.

The externally applied magnetic field 152 is preferably the result of positioning an external magnet 154 on the surface of the patient's skin in proximity to the casing that contains the control unit 102. The external magnet 152 is specifically configured to produce a magnetic field 152 having the preselected magnitude. As will be described in greater detail below, the processor 110 is configured to only initiate a preprogrammed activity when the value of the magnetic field signal is indicative of the presence of the magnetic field 152 having the preselected magnitude.

Figure 2A:
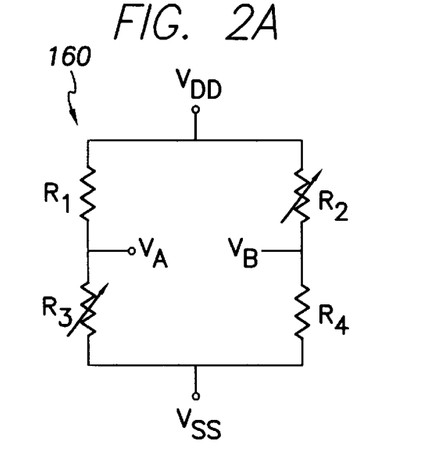
FIG. 2A is an electrical block diagram illustrating one configuration of the magnetoresistive sensor of FIG. 1.

FIG. 2 is an electrical schematic which illustrates a bridge circuit 160 that comprises the portion of the magnetic sensor 150 of FIG. 1. In particular, the bridge circuit 160 of this embodiment receives a supply voltage $V_{DD}$ and a ground voltage $V_{SS}$ with two parallel sets of two resistors in series $R_1$ and $R_3$, and $R_2$ and $R_4$, respectively. The output voltages of the bridge $V_A$ and $V_B$ is obtained at a point between the series resistors $R_1$ and $R_3$, and $R_2$ and $R_4$, respectively.

As shown in FIG. 2, the resistors $R_2$ and $R_3$ are comprised of resistors made of magnetoresistive material and, in particular, are resistors that are made of giant magnetoresistive ratio (GMR) materials. The two resistors $R_2$ and $R_3$ exhibit a magnetoresistive effect whereby the measured resistance values of the resistors $R_2$ and $R_3$ change in response to changes in the magnitude of an applied magnetic field. This change in the resistance of $R_2$ and $R_3$ results in the voltages that are seen at $V_A$ and $V_B$ varying correspondingly.

Hence, application of the external magnetic field 152 to the magnetic field sensor 150 in the previously described manner, results in the magnetoresistive material forming the resistors $R_2$ and $R_3$ having specific resistance values and thereby results in the voltages $V_A$ and $V_B$ also having specific values. A differential voltage signal, $V_A-VB_B$, can therefore be used as the magnetic field signal as this differential voltage signal varies over a range of values depending upon the magnitude of the sensed magnetic field and also has a specific, known value when the bridge circuit 160 is sensing the preselected magnetic field 152 emanating from the external magnet 154.

In the preferred embodiment, the circuit 160 is a giant magnetoresistive sensor bridge that is provided by Nonvolatile Electrics, Inc. of Eden Prairie, MN and is sold under the series designation NVSI. The magnetoresistive elements comprising the resistors $R_2$ and $R_3$ are preferably positioned within a flux concentrator so that the magnetic flux is concentrated on the resistors $R_2$ and $R_3$ thereby allowing the circuit 160 to saturate at fields smaller than the saturation value of the GMR material.

Figure 2B:
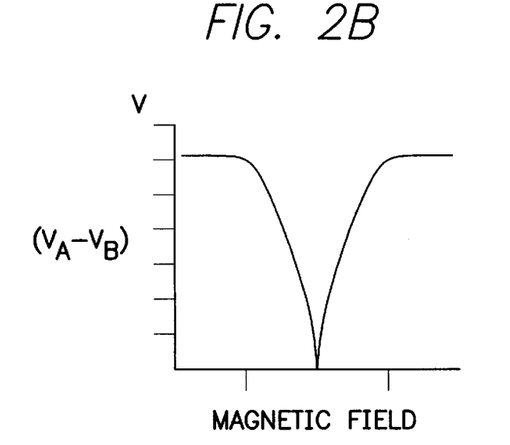
FIG. 2B is a reproduced schematic illustrating a typical performance curve of the sensor of FIG. 2A.

The typical operating characteristics for the GMR sensor used in this embodiment are reproduced in the drawing labeled FIG. 2B. In particular, the differential output voltage of the bridge circuit 180 in volts is plotted in FIG. 2B versus the applied field wherein the applied field is measured in Oersteds using a model NVS 5B50 device with 1.0 mA, 4.6 volts supply in a constant 25° C. temperature. As shown in FIG. 2B, the output signal from the bridge circuit 160 is linear for approximately 70% of the full range of applied fields and the maximum signal occurs at the saturation level of the device.

Using a device having characteristics similar to the characteristics shown in FIG. 2B, the external magnet 154 can be selected so that the magnitude of the magnetic field 152 is in the linear portion of the curve shown in FIG. 2B. For example, the magnet can be selected to have an approximately 35 Oersted field at the implanted sensor 150 so that the resulting differential voltage $V_A$ minus $V_B$ is optimally 0.15 volts using a bridge circuit 160 having characteristics similar to the characteristics shown in FIG. 2B. Magnetic fields which have a magnitude less than the approximately 35 Oersted field results in the circuit 160 outputting a differential voltage $V_A-V_B$ that is less than the optimum 0.15 volts and a significantly stronger magnetic field results in the bridge circuit 160 outputting a voltage that is significantly larger than the optimum voltage of 0.15 volts.

Figure 3:
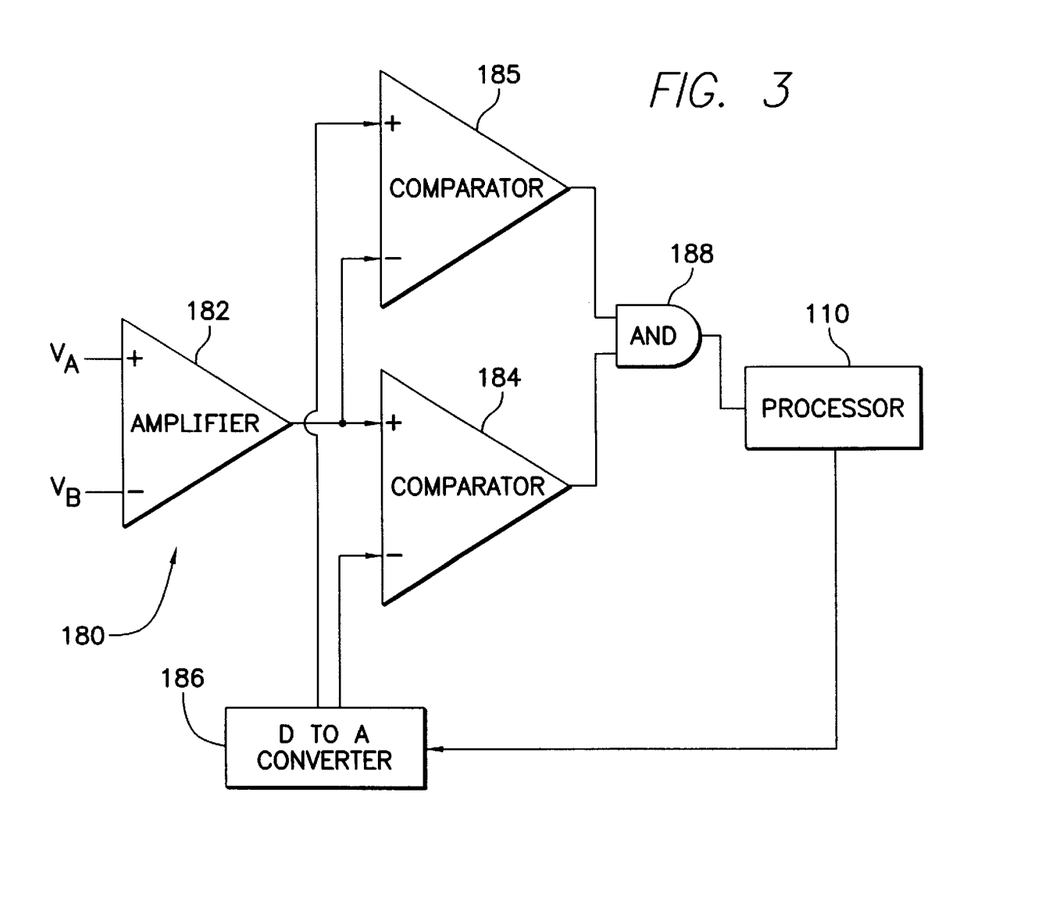
FIG. 3 is an electrical schematic which illustrates a threshold setting circuit forming a portion of the magnetoresistive sensor of the implantable electrical device of FIG. 1.

FIG. 3 illustrates one possible threshold circuit 180 that is a component of the magnetic filed circuit 150. The threshold circuit 180 is used to determine whether the differential output voltage $(V_A-V_B)$ from the bridge circuit 160 comprising the magnetic field signal is within thresholds that are setable by a treating physician. In particular, the output voltages $V_A$ and $V_B$ are initially fed into an amplifier 182 and the amplified differential output signal is then provided to both a first comparator 184 and a second comparator 185. The first comparator 184 compares the amplified differential output signal from the amplifier 182 with a preselected low threshold signal that is provided by a digital to analog converter 186. The second comparator 185 compares the amplified differential output signal from the amplifier 182 to a preselected high threshold signal that is provided by the digital to analog converter 186.

The digital to analog converter 186 provides comparison threshold signals based upon digital signals that are provided from the processor 110. Specifically, the processor 110 is configured to induce the digital to analog converter 186 to provide one or more threshold values to the comparators 184 and 185. The threshold values are selected so that the output from the comparators 184 and 185 indicates whether the magnetic field signal has a value which indicates the sensed magnetic field has a magnitude which corresponds to the known magnitude of the magnetic field 152 produced by the magnet 154.

The value of the threshold signals are determined in response to a treating physician downloading the threshold values to the processor 110 via the external programmer 142 and the telemetry circuit 140. Hence, the treating physician is capable of selecting a range of values that are preferably selected to correspond to the known magnitude of the magnetic field 152 produced by the magnet 150. The comparators 184 and 185 use these values to determine whether the magnetic field signal provided by the bridge circuit 160 is within the preselected range. In the embodiment shown in FIG. 3, the output of the comparators 184 and 185 are provided to a logical AND gate 188 so that the processor 110 only receives a positive signal when the magnetic field signal is within the threshold range that has been selected by the treating physician to correspond to the known magnitude of the magnetic field 152 produced by the magnet 154.

The processor 110 and the threshold circuit 170 are therefore configured to allow the treating physician to set threshold values that results in the magnetic sensor circuit 150 signaling the processor 110 only when the magnitude of the sensed magnetic field corresponds to the known magnitude of the magnetic field 152 produced by the magnet 154. Hence, using the external programmer 142, the treating physician can set threshold values to filter out signals that occur as a result of different magnetic fields being inadvertently applied to the patient. This reduces the likelihood that the processor 110 will inadvertently initiate a preprogrammed activity as a result of some extraneous magnetic field.

For example, the threshold values that are selected by the treating physician and programmed into the processor 110 can be selected so that magnetic fields which are significantly stronger than the magnetic field 152 produced by the external magnet 154, e.g., such as magnetic field resulting from MRI machines, will not result in the processor 110 initiating the preprogrammed activity. Similarly, the threshold values in the comparators 184 and 185 can also be selected so that very low level magnetic fields received by the magnetic field circuit 150 will also not result in the processor 110 initiating the activity.

While the foregoing description has described the evaluation of the magnetic field signal as being performed by discrete circuit components, it will be appreciated that the magnetic field signal can also be supplied directly to the processor 110. The processor 110 could then use a software based solution to determine if the magnetic field signal was within a preselected threshold range indicating that it corresponds to the magnetic field 152. Similarly, it may not be necessary to have both low and high threshold values, rather a single threshold for the magnetic field signal may also be used without departing from the spirit of the present invention.

Figure 4:
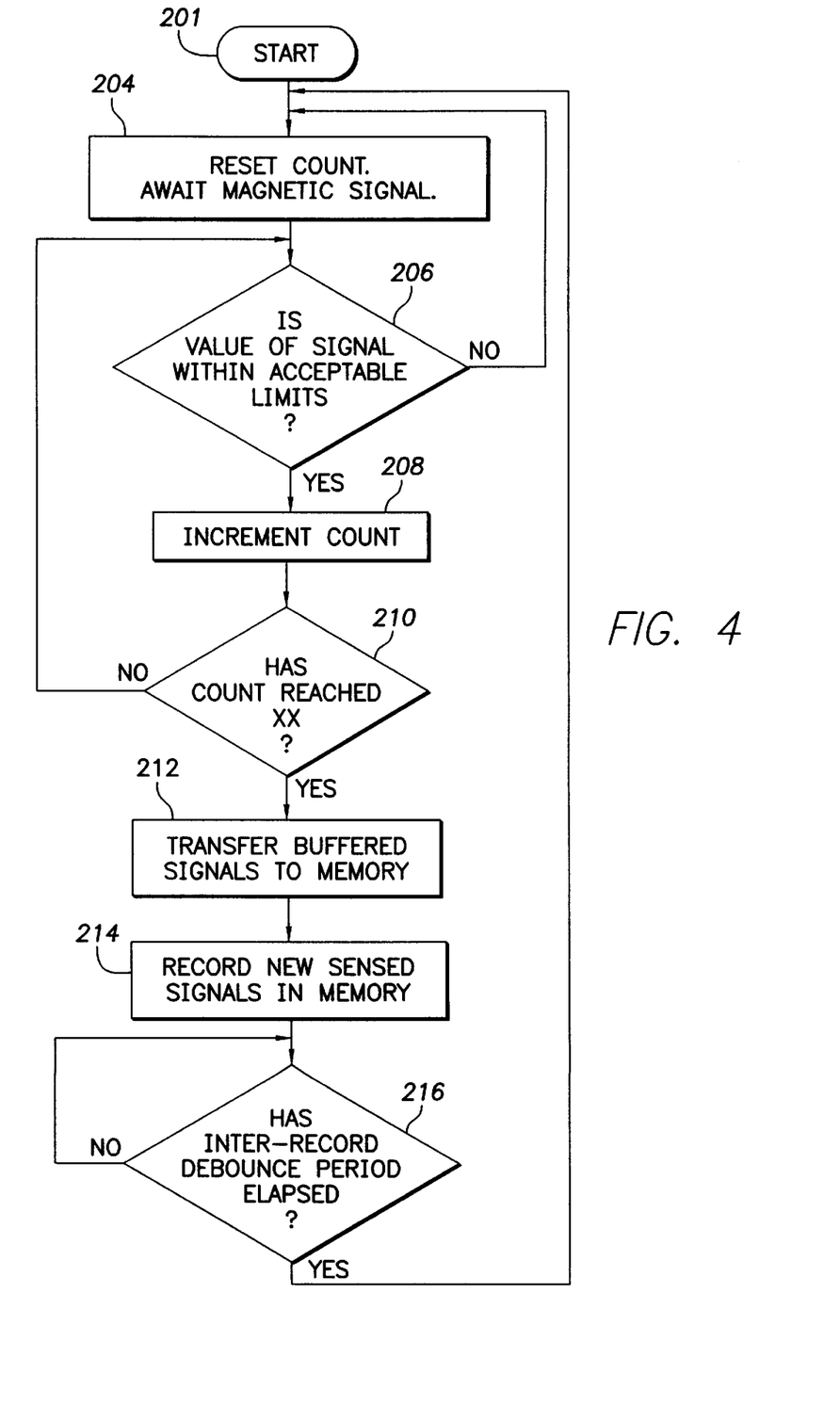
FIG. 4 is a flowchart illustrating the operation of the control unit of the implantable electrical device of FIG. 1 as it enables a record function in response to sensing the externally applied magnetic field.

The processor 110 is preferably programmed so that upon receiving a signal from the magnetic field sensor 150 the processor initiates a preprogrammed activity such as initiating a specified function or initiating a change in the mode of operation of the implantable electrical device 100. FIG. 4 is an exemplary flowchart illustrating the operation of the control unit as it performs a record or "snapshot" function 200 in response to receiving a positive signal from the magnetic field threshold circuit 180. In particular, the processor 110 proceeds from a start state 201 to state 204 to await a signal from AND gate 180 of the magnetic threshold circuit 180, which is indicative of the presence of the magnetic field 152 created by the external magnet 154. Specifically, the control unit 102, and in particular the comparators 184 and 185 described above in reference to FIG. 3, determine, in decision state 206, whether the magnetic field signal is within a preselected threshold range corresponding to the magnetic field 152 of the magnet 154. In the event that the magnetic field signal is within the preselected threshold range, the processor 110 receives an indication from the AND gate 188 that the sensed magnetic field has a magnitude that corresponds to the magnitude of the magnetic field 152 that occurs as a result of the external magnet 154 being positioned adjacent the magnetic field sensor 150.

In this embodiment, the processor 110 then proceeds to transfer buffered signals that were received from the sensor 120 into the memory 130. Specifically, in this embodiment, the sensor 120 continuously provides an intracardiac electrogram (IEGM) signal to the processor 110 and a portion of this signal is buffered. For example, the processor 110 buffers approximately the preceding twenty heartbeat signals received from the sensor 120. This buffered window provides an indication of the function of the heart 103 during the previous heartbeats. These buffered signals are then transferred, in state 210, to the memory 110 in response to the detection of the magnetic field 152 emanating from the external magnet 154. The processor 110 in state 212 then preferably records a preselected number of new heartbeat signals that are provided by the sensor 120 via the sensing circuit 122. The processor 110 then repeats this process until it determines in decision state 214 that the record process 200 is complete. The control unit 102 then returns to state 204 to await the next initiation of the record function 200.

Hence, the processor 110 can be activated to record the sensed performance of the heart 103 for a preselected period of time or a preselected window of heartbeats by positioning the external magnet 154 over the magnetic field sensor 150. This allows the patient to instruct the processor 110 to record the function of the heart 103 when the patient is experiencing physical sensations which indicate that the heart or the implanted device is performing abnormally. These signals can then be subsequently downloaded via the telemetry circuit 140 to the external programmer 142 by the treating physician in a well known manner. The treating physician can thereby retrieve and analyze the event that was noted by the patient.

Since the magnetic sensor circuit 150 incorporates magnetoresistive elements, the record function 200 of the processor 110 is preferably only implemented by the processor 110 in response to the positioning of the external magnet 154 in a location proximate to the implanted magnetic field sensor 150. The function 200 is therefore less likely to be inadvertently initiated in response to the patient being exposed to other magnetic fields as the magnetic field sensor 150 can be set so as to provide a positive output signal only in response to detecting a magnetic field within given values.

While FIG. 4 describes the processor 110 implementing a function whereby heart performance is recorded at the initiation of the patient, the processor 110 can be programmed to implement any of a number of different functions after sensing the presence of the magnetic field 152. For example, the magnetic sensor 150 may be used to initiate a battery test function or a diagnostic function. Further, the physician may use both the telemetry circuit 140 and the magnetic field sensor 150 to initiate diagnostic functions in the system 100 whereby different test therapies are applied to the heart.

Figure 5:
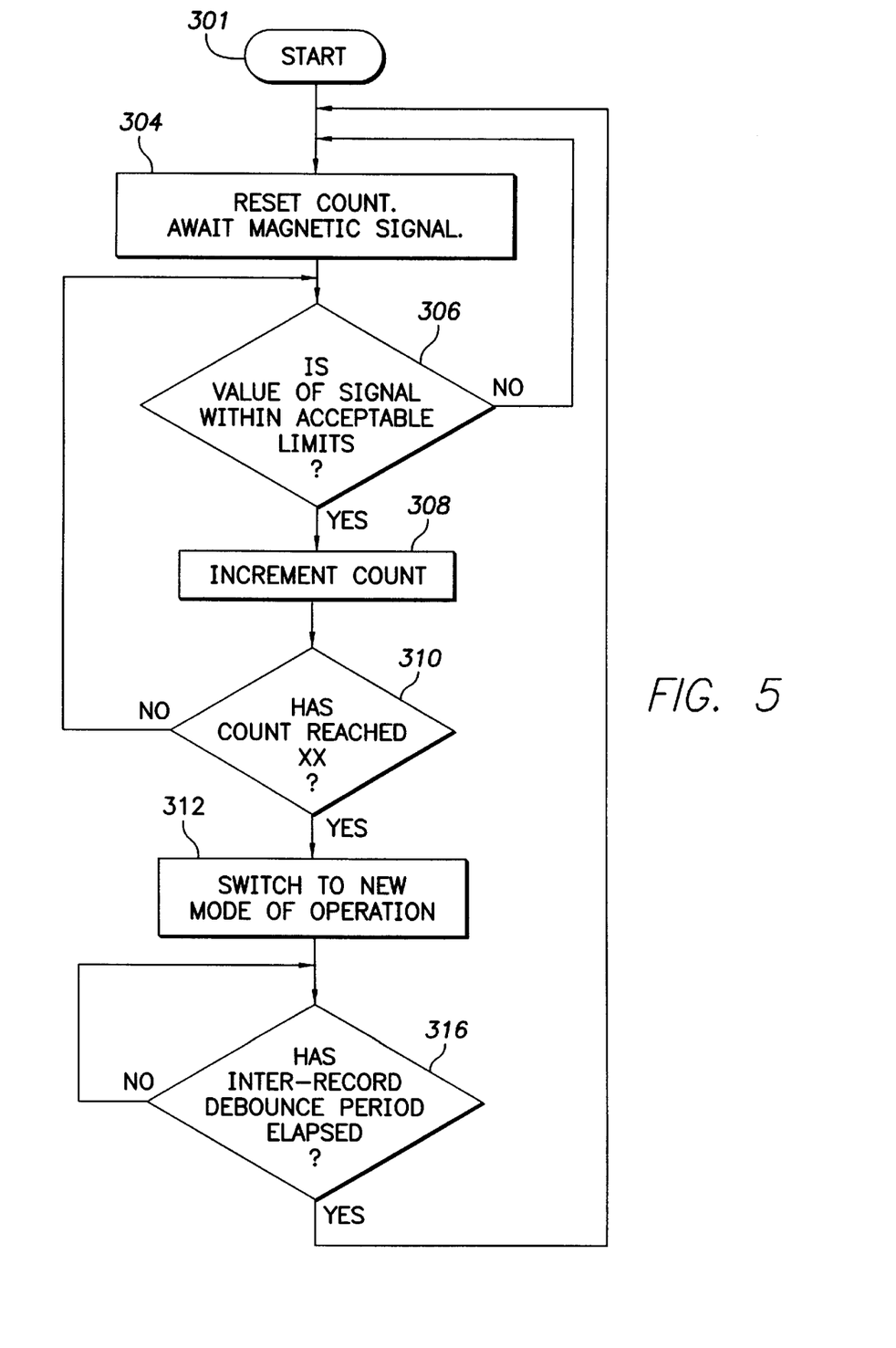
FIG. 5 is a flowchart illustrating the operation of the control unit of the implantable electrical device of FIG. 1 as it implements a change of mode of operation in response to the sensed externally applied magnetic field.

FIG. 5 is a flowchart which illustrates another use of the output signal from the magnetic field sensor 150. In particular, the processor 110 may be programmed so that upon receiving a positive signal from the magnetic field sensor 150, the processor 110 changes the mode of operation of the implantable electrical device. In particular, the processor 110 proceeds from a start state 301 to state 304 where it awaits the magnetic field signal in the manner described above in reference to FIG. 4. Upon receipt of a magnetic field signal, the processor 110 and the comparator circuit 180 discussed in reference to FIG. 3, then determines in decision state 306 whether the magnetic field signal is within the selected threshold range so as to be indicative of the sensing of the magnetic field 152 produced by the external magnet 154. Upon determining that the signal meets the threshold values and is indicative of the magnetic field 152 produced by the external magnet 154, the processor 110 then changes the mode of operation of the implantable electrical device in state 310.

As is understood in the prior art, pacemakers such as the Affinity DR Model 5334 Pacemaker produced by Pacesetter, Inc. of Sylmar, Calif. has a plurality of different mode settings. These mode settings include demand pacing and non-demand pacing. A treating physician using the telemetry circuit 140 can program the processor to change to a different mode of operation in response to the patient positioning the magnet 154 in proximity the sensor 150. This will then result in the device operating in the new mode of operation until the selected magnetic field signal occurs again or until the processor 110 is reprogrammed via the telemetry circuit 140.

From the foregoing, it will be apparent that the implantable electrical device incorporating the magnetic field sensor which provides a signal which is indicative of the magnitude of the magnetic field allows for the implantable electrical device to be programmed to only implement a preprogrammed activity when the signal corresponds to preselected thresholds. The thresholds can be selected so that the function is only triggered upon the sensing of a magnetic field of a particular magnitude which corresponds to the magnitude of the field produced by a preselected external magnet which is positioned adjacent the implanted magnetic field sensor.

Further, the use of magnetoresistive elements as opposed to mechanical devices enhances the reliability of the magnetic field sensor. It will be appreciated that since the magnetic field sensor of the preferred embodiment uses magnetoresistive elements to detect the strength of the magnetic field that the difficulties associated with the moving mechanical parts of the reed switch is reduced.

Although the foregoing description of the preferred embodiment of the present invention has shown, described and pointed out the fundamental novel features of the invention, it will be understood that various omissions, substitutions and changes in the form of the detail of the apparatus as illustrated as well as the uses thereof, may be made by those skilled in the art without departing from the spirit of the present invention. Consequently, the scope of the invention should not be limited to the foregoing discussion, but should be defined by the appended claims.

What is claimed is:

1. An implantable stimulation device, comprising:

storing means for storing instructions for a first mode of operation and a second mode of operation;

magnetic field discriminating means for sensing magnetic field signals, for detecting the presence of an externally applied magnet corresponding to magnetic field signals within a predetermined range of magnetic field magnitudes having a lower limit and an upper limit, and for rejecting extraneous magnetic field signals having a magnetic field magnitude outside of the predetermined range; and control means, responsive to the magnetic field discriminating means and the storing means, for controlling the delivery of stimulation therapy to a patient's heart in the first mode of operation when the magnet is not detected and in the second mode of operation when the magnet is detected.

2. The device of claim 1, further comprising:
means for defining the first mode of operation based on the patient's therapy needs; and
means for defining the second mode of operation based on the patient's diagnostic needs.

3. The device of claim 2, wherein:
the means for defining the second mode of operation based on the patient's diagnostic needs is programmable by an external programmer.

4. The device of claim 2, further comprising:
a battery for providing power to the control means, the storing means and the magnetic field discriminating means;
battery status circuitry, coupled to the battery, for determining battery status; and
wherein the means for defining the second mode of operation based on patient's diagnostic needs comprises means for defining a magnet rate of operation indicative of the battery status.

5. The device of claim 2, further comprising:
a sensing means for sensing cardiac signals;
a telemetry means for providing communication between the control means and an external programmer; and
wherein the means for defining the second mode of operation based on the patient's diagnostic needs comprises means for storing the sensed cardiac signals;
whereby the storage of cardiac signals may be enabled by the application of a magnet by the patient which can be subsequently downloaded by the telemetry means to an external programmer.

6. The device of claim 1, wherein the magnetic field discriminating means further comprises:
a magnetic field sensor, responsive to the magnetic field signals, that produces an output voltage corresponding to the magnitude of the magnetic field signals; and
a threshold circuit, coupled to the magnetic field sensor, that determines whether the output voltage is within an upper threshold voltage and a lower threshold voltage corresponding to the predetermined range of magnetic field magnitudes that occurs when the magnet is externally applied;
whereby extraneous magnetic field signals having a magnetic field magnitude outside of the predetermined range are rejected.

7. The device of claim 6, further comprising:
means for programmably adjusting the upper and lower threshold voltages so as to optimize the sensing of the externally applied magnet and the rejection of extraneous magnetic field signals.

8. The device of claim 6, wherein the magnetic field sensor comprises:
a magneto-resistive element having a resistance which changes in response to variations in the magnitude of the magnetic field signals.

9. The device of claim 8, wherein the magnetic field sensor further comprises:
a bridge circuit that has a first set of two resistors in series, the first set being in parallel with a second set of two resistors in series, wherein one of the two resistors in both the first and the second sets are comprised of magneto-resistive elements made of a giant magneto-resistive ratio (GMR) material, each of the sets of resistors having a center tap across which a differential output voltage is produced which corresponds to the magnitude of the magnetic field signal.

10. An implantable stimulation device, comprising:
a pulse generator circuit that generates stimulation pulses in one of a first mode of operation and a magnet mode of operation;
magnetic field detection circuit that detects magnetic field signals within a predetermined range of magnetic field magnitudes having a lower limit and an upper limit corresponding to the application of a magnet, and rejects extraneous magnetic field signals having a magnetic field magnitude outside of the predetermined range; and
control circuitry, coupled to the pulse generator and responsive to the magnetic field detection circuit, that controls the pulse generator circuit to generate stimulation pulses in the first mode of operation when the application of the magnet is not detected and to operate in the magnet mode of operation when the application of the magnet is detected.

11. The device of claim 10, wherein the magnetic field detection circuit further comprises:
a magneto-resistive sensor that produces resistance changes as a result in variations in the magnetic field signals and further produces an output voltage corresponding to the magnitude of the magnetic field signal; and
a threshold circuit, coupled to the magneto-resistive sensor, that determines whether the output voltage is within a predetermined range of voltages corresponding to the application of the externally applied magnet;
whereby extraneous magnetic field signals having a magnetic field magnitude outside of the predetermined range are rejected.

12. The device of claim 11, wherein the threshold circuit comprises:
a voltage reference circuit that produces a high and a low reference voltage corresponding to the highest and the lowest magnetic field signal for the predetermined range of magnetic field signals indicative of the externally applied magnet;
a first comparator that compares the output voltage of the magnetic field sensor to the high reference voltage;
a second comparator that compares the output voltage of the magnetic field sensor to the low reference voltage; and
logic means for determining that the output voltage of the magnetic field sensor is less than the high reference voltage and is greater than the low reference voltage.

13. The device of claim 12, wherein the voltage reference circuit includes means for programmably adjusting the high and low reference voltages so as to optimize the sensing of the externally applied magnet and the rejection of extraneous magnetic field signals.

14. The device of claim 13, wherein the voltage reference circuit is a programmable digital-to-analog converter.

15. The device of claim 12, wherein the magnetic field sensor comprises:
a bridge circuit that has a first set of two resistors in series, the first set being in parallel with a second set of two resistors in series, wherein one of the two resistors in both the first and the second sets are comprised of resistors made of a giant magnetoresistive ratio (GMR) material, each of the sets of resistors having a center tap across which the output voltage is produced which corresponds to the magnetic field signal.

* * * * *